United States Patent
Apeler et al.

(10) Patent No.: US 6,506,590 B1
(45) Date of Patent: Jan. 14, 2003

(54) PLASMIDS, THEIR CONSTRUCTION AND THEIR USE IN THE MANUFACTURE OF INTERLEUKIN-4 AND INTERLEUKIN-4 MUTEINS

(75) Inventors: Heiner Apeler, Wuppertal (DE); Hermann Wehlmann, Wuppertal (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/483,419

(22) Filed: Jan. 14, 2000

(30) Foreign Application Priority Data

Jan. 20, 1999 (EP) ............................................. 99100967

(51) Int. Cl.$^7$ ........................ C07H 21/04; C12N 15/11; C12N 15/63; C12N 1/20
(52) U.S. Cl. .................... 435/252.33; 435/6; 435/320.1; 435/252.3; 435/252.8; 435/252.1
(58) Field of Search ...................... 435/6, 320.1, 252.3, 435/252.8, 252.1, 252.33

(56) References Cited

U.S. PATENT DOCUMENTS

| | | | |
|---|---|---|---|
| 4,689,406 A | 8/1987 | Banks et al. | 536/27 |
| 5,362,646 A | 11/1994 | Bujard et al. | 435/252.33 |

FOREIGN PATENT DOCUMENTS

| | | | |
|---|---|---|---|
| EP | 0241446 | 10/1987 | C12N/15/00 |
| WO | 9608572 | 3/1996 | C12N/15/68 |
| WO | 9803654 | 1/1998 | C12N/15/24 |

OTHER PUBLICATIONS

Amann, E.; Ochs, B.; Abel, K.–J., "Tightly Regulated Tac Promoter Vectors Useful for the Expression of Unfused and Fused Proteins in *Escherichia coli*", Gene 69: 301–315 (1998).

Apeler, H.; Gottschalk, U.; Guntermann, D.; Hansen, J.; Mässen, J.; Schmidt, E.; Schneider, K.–H.; Schneidereit, M.; Rübsamen–Waigmann, H., "Expression of Natural and Synthetic Genes Encoding Herpes Simplex Virus 1 Protease in *Escherichia coli* and Purification of the Protein", Eur. J. Biochem. 247: 890–895 (1997).

Balbas, P.; Bolivar, F., "Design and Construction of Expression Plasmid Vectors in *Escherichia coli*", Methods in Enzymology 185: 14–37 (1990).

Barany, F., "Single–stranded Hexameric Linkers: A System for In–phase Insertion Mutagenesis and Protein Engineering", Gene 37: 111–123 (1985).

Bujard, H.; Gentz R.; Lanzer, M.; Stueber, D.; Mueller, M.; Ibrahimi, I.; Haeuptle M.–T.; Dobberstein, B., "A T5 Promoter–Based Transcription–Translation System for the Analysis of Proteins in Vitro and in Vivo", Methods in Enzymology 155: 416–433 (1987).

Deng, W. P.; Nickoloff, J. A., "Site–Directed Mutagenesis of Virtually Any Plasmid by Eliminating a Unique Site", Analytical Biochemistry 200: 81–88 (1992).

Hannig, G.; Makrides, S. C.; "Strategies for Optimizing Heterologous Protein Expression in *Escherichia coli*", Trends in Biotechnology 16(2): 54–60 (Feb. 1998).

Hanssens, F.; Martena, N.; Devos, R.; Remaut, E.; Fiara, W., "Expression, Renaturation and Purification of Murine Interleukin 4 from *E. Coli*", Medelingen Van De FAculteit Landbouwwetenschappen Universiteit Gent 57(4b): 2053–2061 (1992).

Kruse, N.; Tont; H.–P.; Sebald, W., "Conversion of Human Interleukin–4 Into a High Affinity Antagonists by a Single Amino Acid Replacement", Embo J. 11(9): 3237–3244 (1992).

Levine, A. D.; Rangwala, S. H.; Horn, N. A.; Peel, M. A.; Matthews, B. K.; Leimgruber, R. M.; Manning, J. A.; Bishop, B. F.; Olins, P. O., "High Level Expression and Refolding of Mouse Interleukin 4 Synthesized in *Escherichia coli*", J. Biol. Chem. 270(13): 7445–7452 (Mar. 1995).

Mosmann, T. R.; Sad, S., "The Expanding Universe of T–Cell Subsets: Th1, Th2 and More", Immunology Today 17(3): 138–146 (Mar. 1996).

Olins, P. O.; Devine, C. S.; Rangwala, S. H.; Kavka, K. S., "The T7 Phage Gene 10 Leader RNA, a Ribosome–Binding Site that Dramatically Enhances the Expression of Foreign Genes in *Escherichia coli*", Gene 73: 227–235 (1988).

Pace, H. C.; Kercher, M. A.; Lu, P.; Markiewicz, P.; Miller, J. H.; Chang, G.; Lewis, M., "Lac Repressor Genetic Map in Real Space", TIBS 22: 334–339 (1997).

Ptitsyn, L. R.; Al'tman, I. B., "Recombinant *Escherichia coli* Strains Provide High–Level Expression of Human Interleukin–3 and Interleukin–4", Bulletin of Experimental Biology and Medicine 119(1): 77–79 (Jan. 1995).

Ryan, J. J., "Interleukin–4 and its Receptor: Essential Mediators of the Allergic Response", J. Allergy and Clin. Immunol. 99(1): 1–5 (1997).

Seed, B.; Aruffo, A., "Molecular Cloning of the CD2 Antigen, the T–Cell Erythrocyte Receptor, by a Rapid Immunoselection Procedure", Proc. Natl. Acad. Sci. USA 84: 3365–3369 (1987).

Sharp, P. M.; Li, W.–H., "The Codon Adaptation Index—A Measure of Directional Synonymous Codon Usage Bias, and its Potential Applications", Nucleic Acid Research 15(3): 1281–1295 (1987).

Stüber, D.; Matile, H.; Garotta, G., "System for High–Level Production in *Escherichia coli* and Rapid Purification of Recombinant Proteins: Application to Epitope Mapping, Preparation of Antibodies, and Structure–Function Analysis", Immunological Methods, I. Lefkovits and B. Pernis, eds., Academic Press, Inc., vol. IV: 121–152 (1990).

Studier, F. W.; Rosenberg, A. H., Dunn, J. J.; Dubendorff, J. W., "Use of T7 RNA Polymerase to Direct Expression of Cloned Genes", Methods in Enzymology 185: 60–89 (Jan. 1990).

Yang, Y.; Yoon, S. R.; Lee, C. E.; Pyun, K. H., "Production, Purification and Immuno–Modulatory Actions of *E. coli*—Derived Recombinant Human Interleukin 4", Korean Biochemical Journal 25(1): 66–72 (1992).

*Primary Examiner*—Sean McGarry
(74) *Attorney, Agent, or Firm*—Susan M. Pellegrino

(57) ABSTRACT

The present invention relates to the construction and use of expression plasmids in the manufacture of recombinant interleukin-4 (IL-4) and interleukin-4 muteins.

3 Claims, 6 Drawing Sheets

Fig. 6

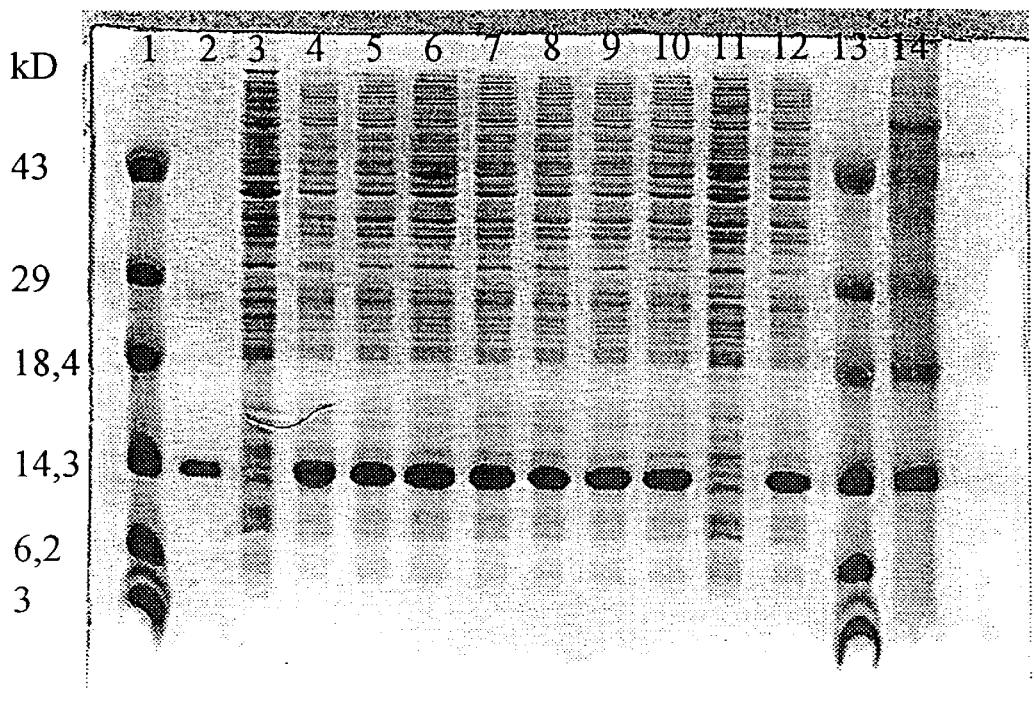

Figure 1:
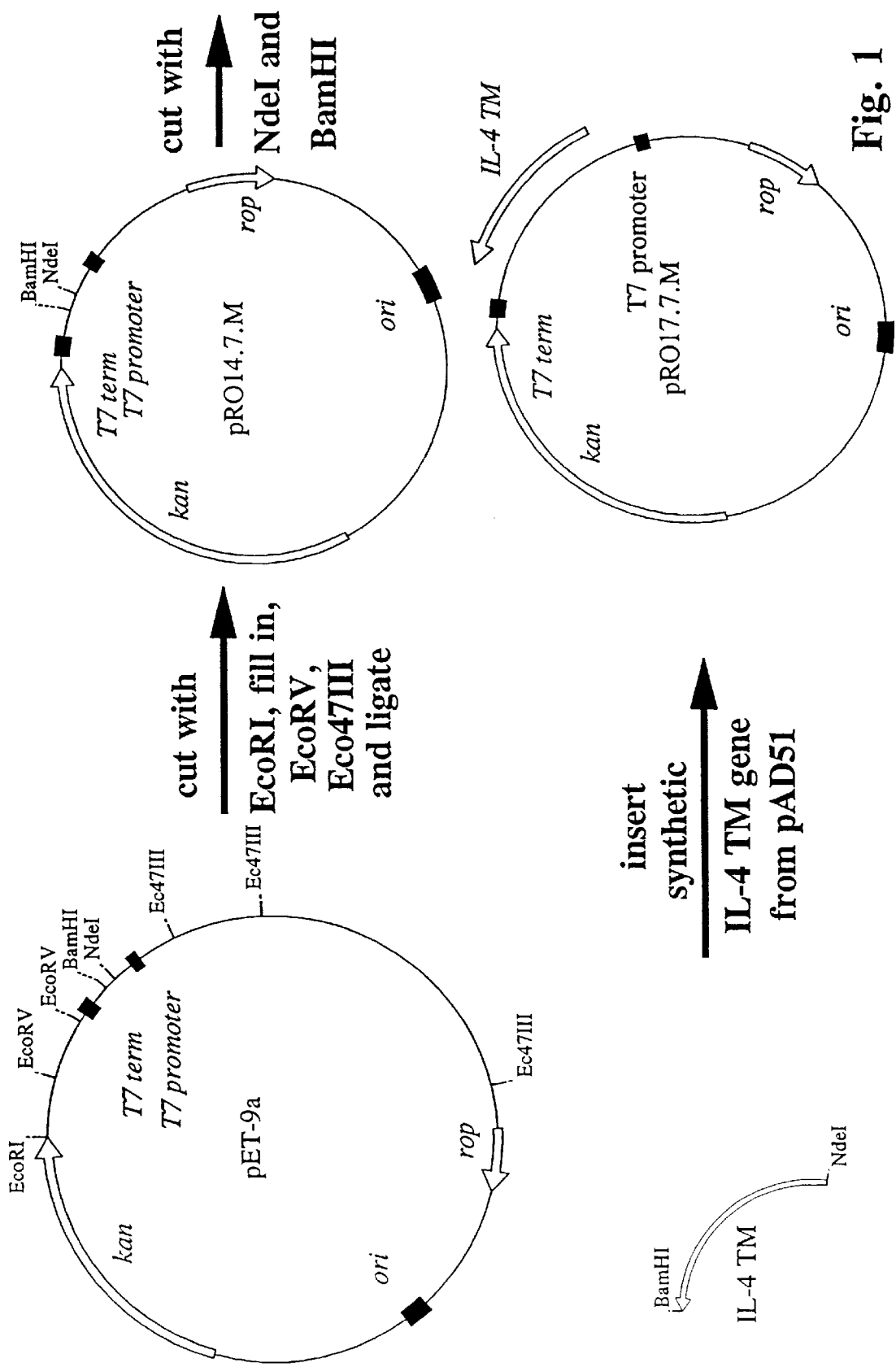
Figure 2:
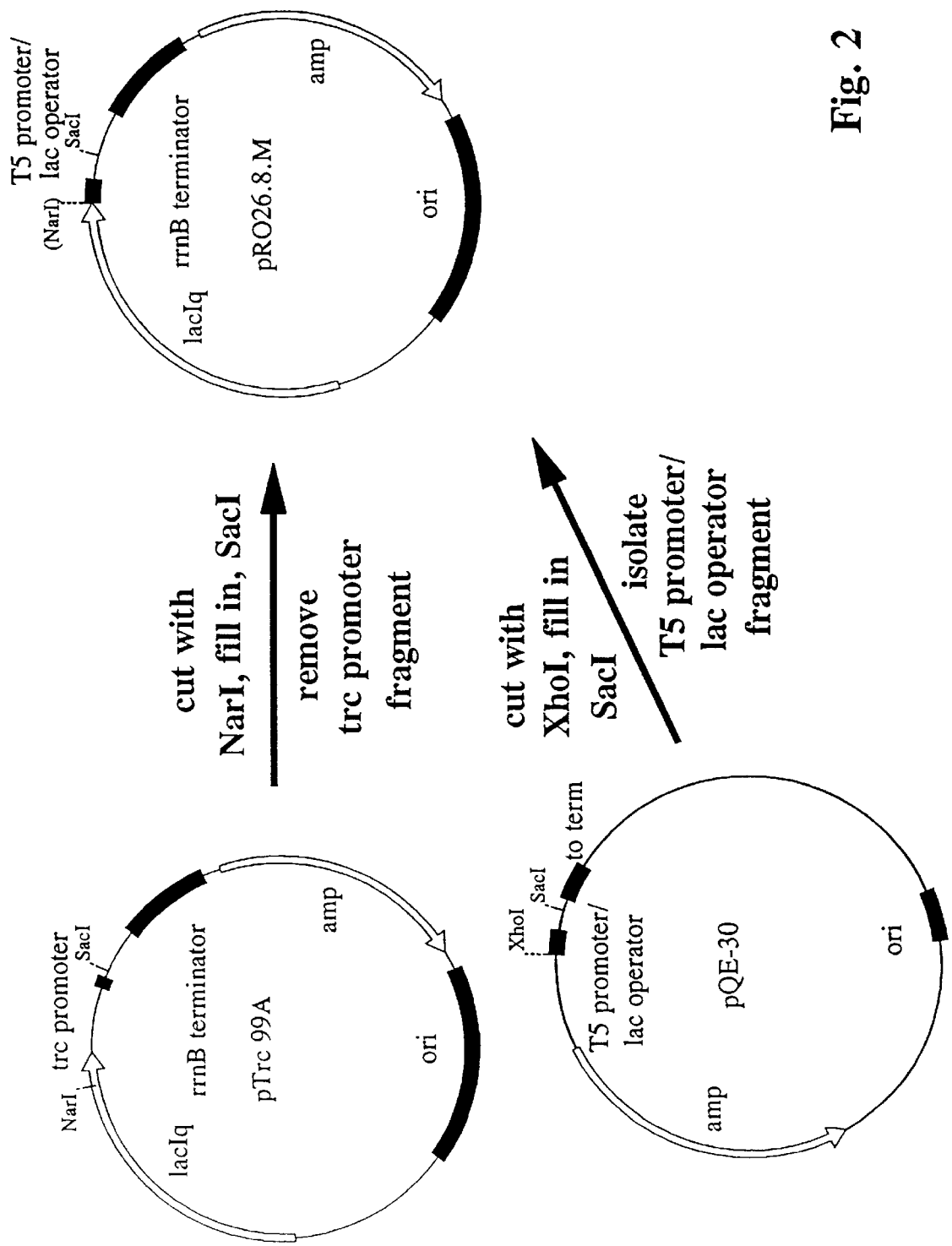
Figure 3:
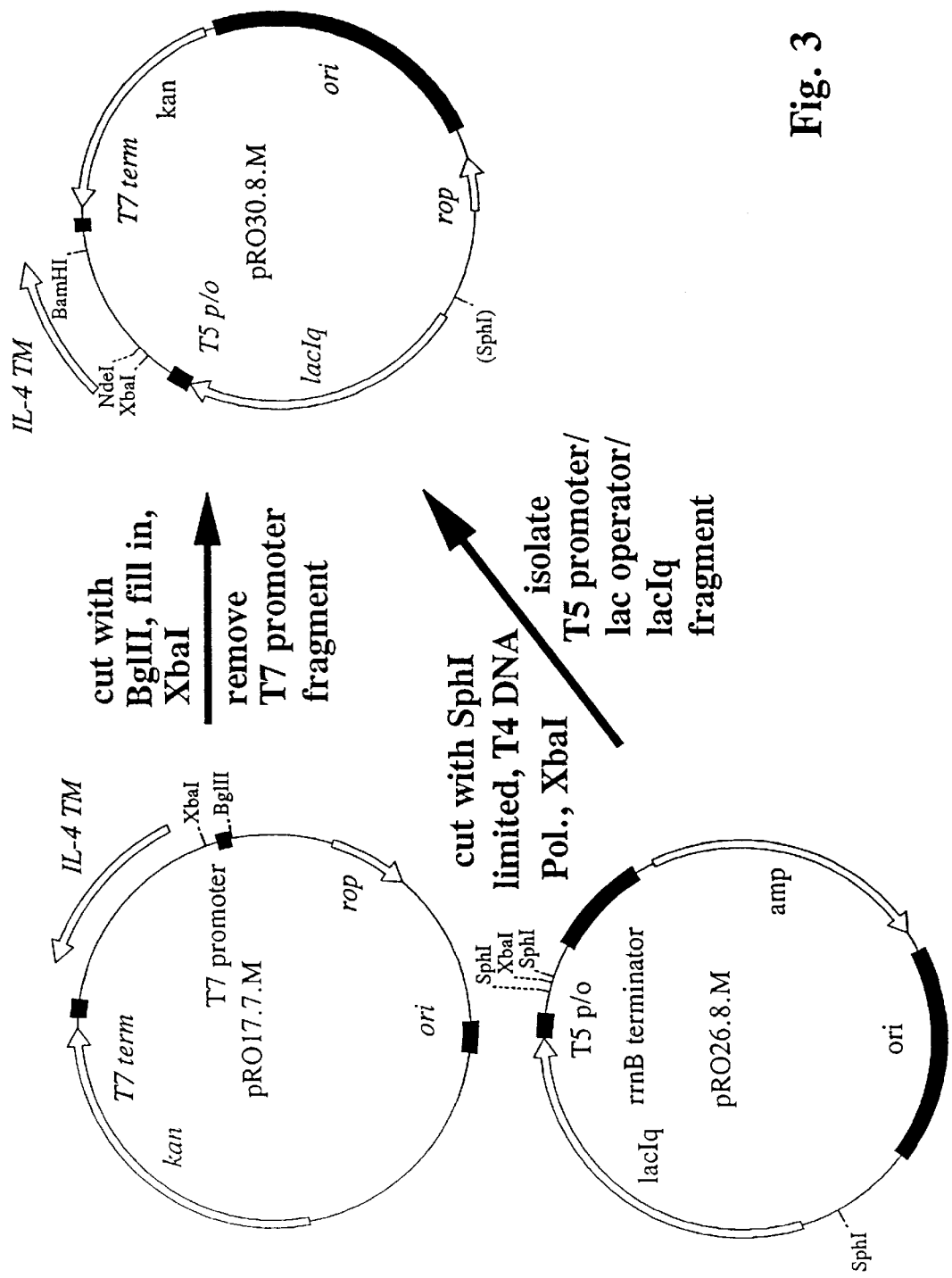
Figure 4:
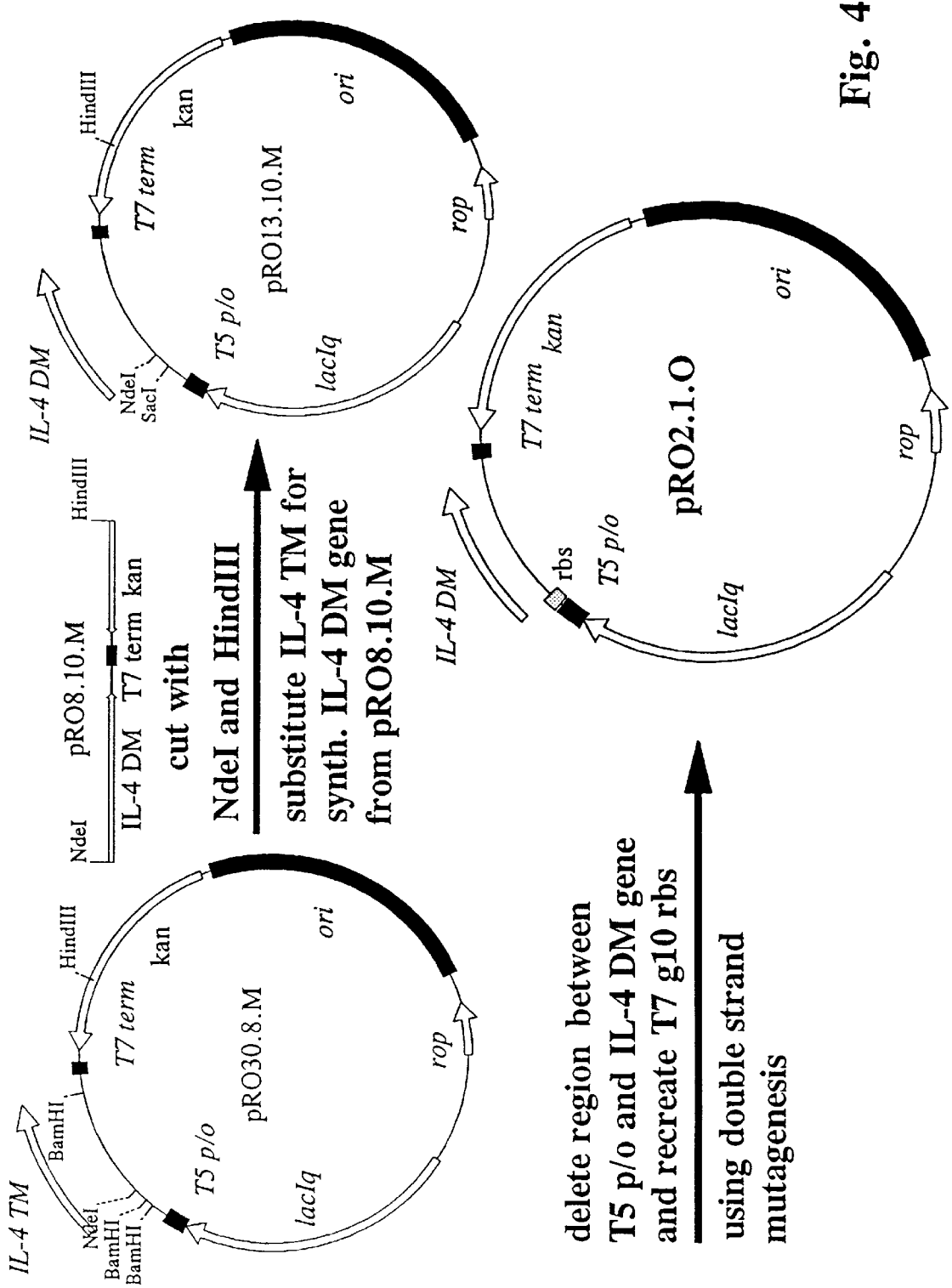

SDS-PAGE (15 %) analysis of total extracts from E. coli/pRO2.1.O grown for different numbers of generations without antibiotic selection after 5 hours of induction with 0,5 mM IPTG. 10 µl of the resuspended cell pellets was applied to each slot. The gel was run under reducing conditions and stained with Coomassie brillant blue.

| | |
|---|---|
| Lane 1: | Molecular weight marker (Low Range, Life Technologies) |
| Lane 2: | IL-4 mutein (5 µg) |
| Lane 3: | E. coli/pRO2.1.O (8 generations) before induction |
| Lane 4: | E. coli/pRO2.1.O (8 generations) after induction |
| Lane 5: | E. coli/pRO2.1.O (18 generations) after induction |
| Lane 6: | E. coli/pRO2.1.O (28 generations) after induction |
| Lane 7: | E. coli/pRO2.1.O (38 generations) after induction |
| Lane 8: | E. coli/pRO2.1.O (48 generations) after induction |
| Lane 9: | E. coli/pRO2.1.O (58 generations) after induction |
| Lane 10: | E. coli/pRO2.1.O (68 generations) after induction |
| Lane 11: | E. coli/pRO2.1.O (78 generations) before induction |
| Lane 12: | E. coli/pRO2.1.O (78 generations) after induction |
| Lane 13: | Molecular weight marker (Low Range, Life Technologies) |
| Lane 14: | Molecular weight marker (High Range, Life Technologies) |

PLASMIDS, THEIR CONSTRUCTION AND THEIR USE IN THE MANUFACTURE OF INTERLEUKIN-4 AND INTERLEUKIN-4 MUTEINS

FIELD OF THE INVENTION

The present invention relates to the construction and use of expression plasmids in the manufacture of recombinant interleukin-4 (IL-4) and interleukin-4 muteins.

BACKGROUND OF THE INVENTION

Mature human interleukin-4 (IL-4) is composed of 129 amino acids with 50% homology to mouse IL-4. IL-4 is the only cytokine known to direct the differentiation of T helper cells to a $TH_{H2}$ phenotype (Mosmann and Sad, Immunol. Today 17, 138–146, 1996). IL-4 signals on lymphocytes and other cells through a heterodimeric complex of two cytokine receptors, the IL4Rα and the common γ-chain (γc). Antagonistic IL-4 mutants have been described (Kruse et al., EMBO J. 11, 3237–3244, 1992). Three amino acids close to the C-terminus (R121, Y124 and S125) are important for binding to the γc-chain. The introduction of Asp (D) into these positions blocks receptor dimerization and transmembrane signaling.

The interleukin-4 double mutein (IL-4 DM) is an IL-4 variant with 2 amino acid changes in position 121 and 124 termed IL-4 R121D Y124D. IL-4 DM is able to block both IL-4 and IL-13 activities. In contrast to all single site mutants no residual agonistic activity has ever been found for this mutein. It is believed that these antagonistic properties of IL-4 DM are useful for the treatment of diseases which involve $T_{H2}$ development and/or IgE production (Ryan, Allergy Clin. Immunol. 99, 1–5, 1997).

As described in various publications, procaryotic organisms can be used to produce recombinant IL-4 and IL-4 muteins. Unfortunately, the described systems have a number of drawbacks (low expression level, low stability of the expression vector) which make large scale production of IL-4 and IL-4 muteins impossible or economically unfeasible.

The main criteria for an efficient and safe expression system are:
  high product yield
  regulatable stable expression
  stability of the expression vector Several features of an expression plasmid are important for the criteria listed above (Hannig et al., TIBTECH. 16, 54–60, 1998). These are:
  Promoter
  Ribosomal binding site (rbs)
  Codon usage of the corresponding gene
  Transcriptional terminator
  Resistance gene
  Regulation of expression
  Origin of replication (ori)

SUMMARY OF THE INVENTION

Expression plasmids for IL-4 and IL-4 muteins with modifications in all of the relevant elements for an efficient and safe expression system were generated. The quality and suitability of the corresponding expression system was ranked mainly according to the following criteria:
  Yield of IL-4 and IL-4 muteins
  Plasmid stability
  Maintenance of induction capability The object of the present invention is, therefore, to make available a process for the construction and use of expression plasmids in the large scale manufacture of recombinant interleukin-4 (IL-4) and interleukin-4 muteins. In addition the newly developed host/vector system should be well suited for the expression of other proteins (cytokines, growth factors, soluble receptors, antibodies etc.).

Surprisingly, it has been found that bacteria transformed with plasmids according to the present invention give expression rates, plasmid and expression stability values many times higher than those observed after transforming the identical hosts with plasmids known in the art. Therefore, the plasmids of this invention are far more useful for the preparation of recombinant interleukin-4 and interleukin-4 muteins than all plasmids previously known.

The newly developed vector system contains the following elements:
T5 Promoter

The *E. coli* phage T5 promoter together with two lac operator sequences is derived from the pQE30 plasmid (Qiagen) belonging to the pDS family of plasmids (Bujard et al., Methods Enzymol. 155, 416–433, 1987 and Stüber et al., Immunological Methods, I. Lefkovits and B. Pernis, eds., Academic Press, Inc., Vol. IV, 121–152, 1990).
T7 g10 Ribosomal Binding Site The ribosomal binding site (rbs) is derived from the region upstream from gene 10 of the phage T7 (T7 g 10 leader). Gene 10 of phage T7 codes for the coat protein, which is the major protein expressed after T7 infection. The T7 g10 rbs was obtained from the vector pET-9a (Studier et al., Methods Enzymol. 185, 60–89, 1990). The T7 g10 leader spans a region of about 100 bp (Olins et al., Gene 227–235, 1988). In the final expression construct the region upstream of the XbaI site is deleted. The T7 g10 leader sequence now spans 42 bp and harbours one base exchange from G to A in position 3638 of the preferred plasmid.
Codon Usage of the Natural IL-4 Sequence As an effective measure of synonymous codon usage bias, the codon adaptation index (CAI) can be useful for predicting the level of expression of a given gene (Sharp et al., Nucleic Acids Res. 15, 1281–1295, 1987 and Apeler et al., Eur. J. Biochem. 247, 890–895, 1997). The CAI is calculated as the geometric mean of relative synonymous codon usage (RSCU) values corresponding to each of the codons used in a gene, divided by the maximum possible CAI for a gene of the same amino acid composition. RSCU values for each codon are calculated from very highly expressed genes of a particular organism, e.g. *E. coli*, and represent the observed frequency of a codon divided by the frequency expected under the assumption of equal usage of the synonymous codons for an amino acid. Highly expressed genes, e.g. genes encoding ribosomal proteins, have generally high CAI values ≧0.46. Poorly expressed genes like lad and trpR in *E. coli* have low CAI values ≦0.3.

The calculated *E. coli* CAI value for the natural IL-4 sequence is 0.733. This means that the natural gene should be well-suited for high level expression in *E. coli*. Nevetheless a synthetic gene with optimal *E. coli* codon usage (CAI value=1) has the potential to further increase the expression level. Therefore synthetic IL-4 and IL-4 mutein genes were designed and cloned.
Transcriptional Terminator A T7 DNA fragment containing the transcription terminator Tϕ is derived from the vector pET-9a (Studier et al., Methods Enzymol. 185, 60–89, 1990). Transcriptional terminators determine the points where the mRNA-RNA polymerase-DNA complex dissociates, thereby ending transcription. The presence of a transcriptional terminator at the end of a highly expressed gene has several advantages: they minimize sequestering of RNA polymerase that might be engaged in unnecessary transcription, they restrict the mRNA length to the minimal, thus limiting energy expense, as strong transcription may interfere with the origin of replication, a transcriptional terminator increases plasmid stability due to copy number maintenance (Balbas and Bolivar, Methods Enzymol. 185, 14–37, 1990).

Resistance Gene

The kan resistance gene is derived from the vector pET-9a (Studier et al., Methods Enzymol. 185, 60–89, 1990). Originally, this is the kan gene of Tn903 from the vector pUC4KISS (Barany, Gene 37, 111–123, 1985). In the preferred plasmid the kan gene and the IL-4 and IL-4 mutein gene have opposite orientations, so there should not be an increase in kan gene product after induction due to read-through transcription from the T5 promoter. Kanamycin was chosen as selective marker because it is the preferred antibiotic for GMP-purposes. In addition, kan gene based vectors are more stable than ampicillin resistant (bla) plasmids. Ampicillin selection tends to be lost in cultures as the drug is degraded by the secreted β-lactamase enzyme. The mode of bacterial resistance to kanamycin relies upon an aminogly-coside phosphotransferase that inactivates the antibiotic.

Regulation of Expression

Controlled gene expression is absolutely necessary for the set-up of a stable plasmid system, particularly if the protein of interest is deleterious to the host cell. The preferred plasmid uses a lac-based inducible system consisting of a lac repressor gene (lacI) and two synthetic lac operator sequences fused downstream to the *E. coli* phage T5 promoter. The lacI$^q$ promoter and the lacI structural gene were isolated from the vector pTrc99A (Amann et al., Gene 69, 301–315, 1988). I$^q$ is a promoter mutation which leads to overproduction of the lacI repressor. The wild-type lac repressor is a tetrameric molecule comprising four identical subunits of 360 amino acids each. The lac repressor tetramer is a dimer of two functional dimers. The four subunits are held together by a four-helix bundle formed from residues 340–360. Due to the isolation of the lacI gene from the vector pTrc99A by a NarI cut the residues beyond amino acid 331 are deleted and 10 amino acids not normally encoded in the lacI gene are added. It is known that mutations or deletions that occur in the C-terminal part of lacI, beyond amino acid 329, result in functional dimers that appear phenotypically similar to the wild-type repressor (Pace et al., TIBS 22, 334–339, 1997).

Origin of Replication (ori)

The origin of replication (ori) of the preferred plasmid is derived from the vector pET-9a, the ori of which originates from pBR322. The preferred plasmid therefore carries the pMB1 (ColE1) replicon. Plasmids with this replicon are multicopy plasmids that replicate in a 'relaxed' fashion. A minimum of 15–20 copies of plasmid are maintained in each bacterial cell under normal growth conditions. The actual number for the preferred plasmid is within this range. Replication of the ColE1-type ori is initiated by a 555-nucleotide RNA transcript, RNA II, which forms a persistent hybrid with its template DNA near the ori. The RNA II-DNA hybrid is then cleaved by RNase H at the ori to yield a free 3'OH that serves as a primer for DNA polymerase I. This priming of DNA synthesis is negatively regulated by RNA I, a 108-nucleotide RNA molecule complementary to the 5'end of RNA II. Interaction of the antisense RNA I with RNA II causes a conformational change in RNA II that inhibits binding of RNA II to the template DNA and consequently prevents the initiation of plasmid DNA synthesis. The binding between RNAs I and II is enhanced by a small protein of 63 amino acids (the Rop protein, Repressor of primer), which is encoded by a gene located 400 nucleotides downstream from the origin of replication (Sambrook et al., Molecular Cloning, Cold Spring Harbor, 1989). Deletion of the rop gene leads to an increase in copy number and due to a gene dosage effect to enhanced expression levels of the plasmid encoded heterologous gene. This observation was also made for the IL-4 expression vectors tested. But it turned out that rop-plasmids are instable and lost very rapidly during fermentation under non-selective conditions. Therefore the replicon of the preferred plasmid contains the rop gene to ensure high plasmid stability. The preferred plasmid lacks the mob gene that is required for mobilization and is therefore incapable of directing its own conjugal transfer from one bacterium to another.

In the preferred plasmid all elements not necessary for plasmid replication, resistance and regulatable expression were deleted.

To fall within the scope of the present invention, not all of the above features have to be incorporated in the construction of the preferred expression plasmid. For example, a natural interleukin-4 or interleukin-4 mutein gene can be used instead of a synthetic one with optimized *E. coli* codon usage. The preferred transcription terminator is Tφ, but other terminators like rrnB T2 or aspA can also be used. Likewise, it is possible to take the elements for the construction of the preferred plasmid from other than the herein described commercially available vectors.

The methods employed in the course of the establishment of the expression system are given below.

Materials and Methods

Enzymes

Restriction endoculeases, calf intestinal alkaline phosphatase, T4 polynucleotide kinase and T4 DNA ligase were purchased from Boehringer Mannheim and GIBCO-BRL and used as recommended by the supplier.

Recombinant DNA Methods

Standard cloning procedures have been described in Sambrook et al. (Molecular Cloning, Cold Spring Harbor, 1989). Transformations were performed according to M. Scott (Seed and Aruffo, Proc. Natl. Acad. Sci. USA 84, 3365–3369, 1987). As hosts for transformations the *E. coli* strains DH5α (GIBCO BRL) and W3110 (ATCC 27325) were primarily used. The genotype of W3110 is K12, F$^-$, [N(rrnD-rrnE)]λ$^-$.

Large scale isolations of plasmid DNA were carried out with Qiagen-tips (Qiagen). Extraction of DNA fragments from agarose gels was performed using Jetsorb (Genomed) as recommended by the supplier.

Oligonucleotides for site directed mutagenesis, PCR reactions and sequencing were obtained from MWG Biotech, Pharmacia Biotech or GIBCO BRL.

The mutagenesis experiments were carried out by the method of Deng and Nickoloff (Deng and Nickoloff, Anal. Biochem. 200, 81–88, 1992) using the 'Unique Site Elimination Mutagenesis' system from Pharmacia Biotech. The primer used for the recreation of the T7 g10 rbs has the following sequence:

5'TCAATTGTGAGCGGATAACAATTTCACACATC
TAGAAATAATTTTGTTTAACTTTAAGAA3'
(Seq.1).

All constructs and DNA sequences were confirmed using Dye Terminator Cycle Sequencing with AmpliTaq DNA Polymerase, FS on an ABI 373A sequencer (Applied Biosystems).

The invention is explained in more detail by the following examples, FIGURES and sequences information:

FIG. 1 to FIG. 4: Construction of the preferred expression plasmid. (Abbreviations: IL-4 TM, IL-4 triple mutein; IL-4 DM, IL-4 double mutein).

Figure 5:
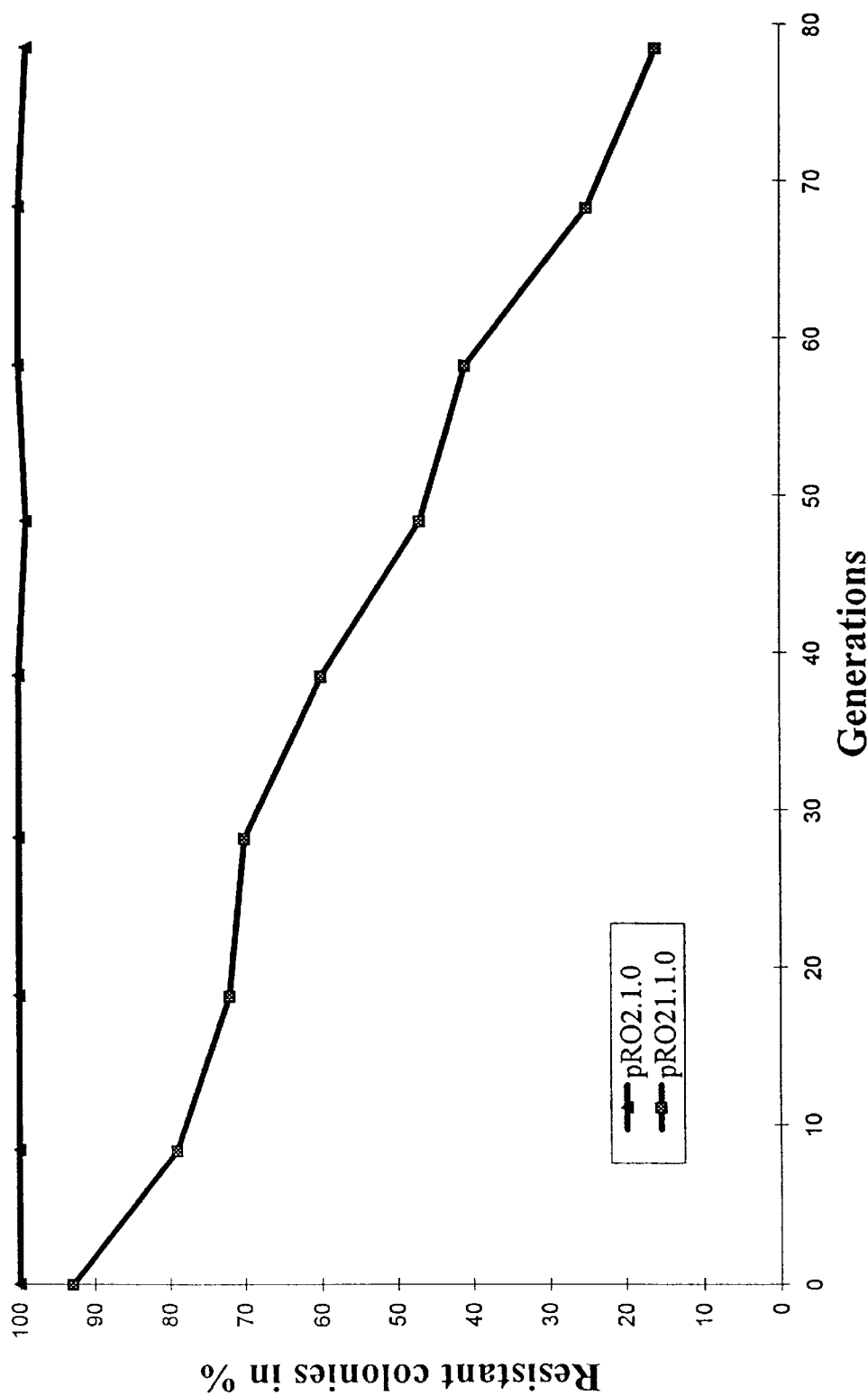

FIG. 5: Plasmid stability of the IL-4 mutein expression vectors pRO21.1.O and pRO2.1.O. The vector pRO2.1.O remains fully stable over 78 generations without antibiotic selection. In contrast the expression vector pRO21.1.O, which is based on the commercially available plasmid pET-30a (Novagen), is lost very rapidly. Only 16% of the colonies contain the plasmid after 78 generations without kanamycin selection.

FIG. 6: Maintenance of induction and expression capability of the preferred IL-4 and IL-4 mutein expression vector.

EXAMPLES

Example 1
Plasmid Stability Test

The plasmid stability tests were always started with a culture frozen in liquid nitrogen. The $OD_{600}$ of the thawed culture was determined, the culture diluted up to $10^{-4}$ in PBS buffer and plated on LB agar plates without antibiotic.

1 ml of the thawed culture was inoculated into 100 ml of peptone medium (30 g Soya peptone, 20 g Yeast extract, 5 g $KH_2PO_4$, 20 g Glycerol, 1 g $MgSO_4 \times 7H_2O$ per liter, pH 7,0) and incubated at 37° C. with 280 rpm for 24 hours.

The $OD_{600}$ of the grown culture was determined, the culture diluted up to $10^{-6}$ in PBS buffer and plated on LB agar plates without antibiotic to get well separated colonies.

100 μl from the grown culture were inoculated into 100 ml peptone medium and incubated at 37° C. with 280 rpm for 24 hours. This procedure was repeated eight times.

100 well separated colonies from the LB plates were gridded onto LB plates with kanamycin (25 μg/ml) and LB plates without kanamycin and incubated at 37° C. overnight. The percentage of resistant colonies was determined on every day.

The number of generations per day were calculated according to the following formula: $\log[OD_{600\ END}/OD_{600\ BEG}]/\log 2$.

For the expression studies 1 ml of a grown culture was diluted 100 fold into LB medium and handled as described (see Example 2).

Example 2
Expression

For small scale expression of interleukin-4 and interleukin-4 muteins cells were grown in LB medium (10 g Bacto tryptone, 5 g Yeast extract, 10 g NaCl per liter, pH 7,5) until OD600 reached 0.8–1.0. Expression was induced by addition of IPTG to a final concentration of 0.5 mM and incubation continued for 5 hours. Cells were harvested by centrifugation.

For SDS-PAGE analysis cell pellets were resuspended in SDS-PAGE loading buffer to a concentration of 1 OD600 unit/100 μl.

What is claimed is:

1. An expression plasmid for the manufacture of IL-4 and IL-4 muteins in a strain of *Escherichia coli,* comprising in 5' to 3' order the following operatively linked elements: a regulatable promoter consisting of the *E. coli* phage T5 promoter and two lac operator sequences, a ribosome binding site from the *E-coli* phage T7 g10, a translational start codon, a structural gene for IL-4 or an IL-4 mutein and downstream of that structural gene one transcription terminator.

2. A plasmid comprising the elements of claim 1, wherein said plasmid is the plasmid pRO2.1.0.

3. An *Escherichia coli* cell transformed with one or more of the plasmids of claim 1 or 2.

* * * * *

SEQUENCE LISTING

<160> NUMBER OF SEQ ID NOS: 2

<210> SEQ ID NO 1
<211> LENGTH: 60
<212> TYPE: DNA
<213> ORGANISM: Unknown
<220> FEATURE:
<223> OTHER INFORMATION: Description of Unknown Organism: primer

<400> SEQUENCE: 1
tcaattgtga gcggataaca atttcacaca tctagaaata attttgttta actttaagaa    60

<210> SEQ ID NO 2
<211> LENGTH: 4202
<212> TYPE: DNA
<213> ORGANISM: Unknown
<220> FEATURE:
<223> OTHER INFORMATION: Description of Unknown Organism: Human

<400> SEQUENCE: 2
ttagaaaaac tcatcgagca tcaaatgaaa ctgcaattta ttcatatcag gattatcaat     60
accatatttt tgaaaagcc gtttctgtaa tgaaggagaa aactcaccga ggcagttcca    120
taggatggca agatcctggt atcggtctgc gattccgact cgtccaacat caatacaacc    180
tattaatttc ccctcgtcaa aaataaggtt atcaagtgag aaatcaccat gagtgacgac    240
tgaatccggt gagaatggca aaagcttatg catttctttc cagacttgtt caacaggcca    300
gccattacgc tcgtcatcaa aatcactcgc atcaaccaaa ccgttattca ttcgtgattg    360
cgcctgagcg agacgaaata cgcgatcgct gttaaaagga caattacaaa caggaatcga    420

-continued

```
atgcaaccgg cgcaggaaca ctgccagcgc atcaacaata ttttcacctg aatcaggata    480
ttcttctaat acctggaatg ctgttttccc ggggatcgca gtggtgagta accatgcatc    540
atcaggagta cggataaaat gcttgatggt cggaagaggc ataaattccg tcagccagtt    600
tagtctgacc atctcatctg taacatcatt ggcaacgcta cctttgccat gtttcagaaa    660
caactctggc gcatcgggct tcccatacaa tcgatagatt gtcgcacctg attgcccgac    720
attatcgcga gcccatttat acccatataa atcagcatcc atgttggaat ttaatcgcgg    780
cctcgagcaa gacgtttccc gttgaatatg gctcataaca ccccttgtat tactgtttat    840
gtaagcagac agttttattg ttcatgacca aaatccctta acgtgagttt tcgttccact    900
gagcgtcaga ccccgtagaa aagatcaaag gatcttcttg atccttttt tttctgcgcg    960 taatctgctg cttgcaaaca aaaaaaccac cgctaccagc ggtggtttgt ttgccggatc    1020
aagagctacc aactcttttt ccgaaggtaa ctggcttcag cagagcgcag ataccaaata    1080
ctgtccttct agtgtagccg tagttaggcc accacttcaa gaactctgta gcaccgccta    1140
catacctcgc tctgctaatc ctgttaccag tggctgctgc cagtggcgat aagtcgtgtc    1200
ttaccgggtt ggactcaaga cgatagttac cggataaggc gcagcggtcg ggctgaacgg    1260
ggggttcgtg cacacagccc agcttggagc gaacgaccta caccgaactg agatacctac    1320
agcgtgagct atgagaaagc gccacgcttc ccgaagggag aaaggcggac aggtatccgg    1380
taagcggcag ggtcggaaca ggagagcgca cgagggagct tccaggggga aacgcctggt    1440
atctttatag tcctgtcggg tttcgccacc tctgacttga gcgtcgattt ttgtgatgct    1500
cgtcaggggg gcggagccta tggaaaaacg ccagcaacgc ggcctttttta cggttcctgg    1560 ccttttgctg gccttttgct cacatgttct ttcctgcgtt atccctgat tctgtggata    1620 accgtattac cgcctttgag tgagctgata ccgctcgccg cagccgaacg accgagcgca    1680
gcgagtcagt gagcgaggaa gcggaagagc gcctgatgcg gtattttctc cttacgcatc    1740
tgtgcggtat ttcacaccgc aatggtgcac tctcagtaca atctgctctg atgccgcata    1800
gttaagccag tatacactcc gctatcgcta cgtgactggg tcatggctgc gccccgacac    1860
ccgccaacac ccgctgacgc gccctgacgg gcttgtctgc tcccggcatc cgcttacaga    1920
caagctgtga ccgtctccgg gagctgcatg tgtcagaggt tttcaccgtc atcaccgaaa    1980
cgcgcgaggc agctgcggta agctcatca gcgtggtcgt gaagcgattc acagatgtct    2040
gcctgttcat ccgcgtccag ctcgttgagt ttctccagaa gcgttaatgt ctggcttctg    2100
ataaagcggg ccatgttaag ggcggttttt tcctgtttgg tcactgatgc ctccgtgtaa    2160
gggggatttc tgttcatggg ggtaatgata ccgatgaaac gagagaggat gctcacgata    2220
cgggttactg atgatgaaca tgcccggtta ctggaacgtt gtgagggtaa acaactggcg    2280
gtatggatgc ggcgggacca gagaaaaatc actcaggggtc aatgccagcg ctcatgagcc    2340
cgaagtggcg agcccgatct tccccatcgg tgatgtcggc gatataggcg ccagcaaccg    2400
cacctgtggc gccggtgatg ccggccacga tgcgtccggc gtagaggatc gagatccatt    2460
tacgttgaca ccatcgaatg gtgcaaaacc tttcgcggta tggcatgata gcgcccggaa    2520
gagagtcaat tcagggtggt gaatgtgaaa ccagtaacgt tatacgatgt cgcagagtat    2580
gccggtgtct cttatcagac cgtttcccgc gtggtgaacc aggccagcca cgtttctgcg    2640
aaaacgcggg aaaagtgga agcggcgatg cggagctga attacattcc caaccgcgtg    2700
gcacaacaac tggcgggcaa acagtcgttg ctgattggcg ttgccacctc cagtctggcc    2760
```

-continued

```
ctgcacgcgc cgtcgcaaat tgtcgcggcg attaaatctc gcgccgatca actgggtgcc      2820
agcgtggtgg tgtcgatggt agaacgaagc ggcgtcgaag cctgtaaagc ggcggtgcac      2880
aatcttctcg cgcaacgcgt cagtgggctg atcattaact atccgctgga tgaccaggat      2940
gccattgctg tggaagctgc ctgcactaat gttccggcgt tatttcttga tgtctctgac      3000
cagacaccca tcaacagtat tattttctcc catgaagacg gtacgcgact gggcgtggag      3060
catctggtcg cattgggtca ccagcaaatc gcgctgttag cgggcccatt aagttctgtc      3120
tcggcgcgtc tgcgtctggc tggctggcat aaatatctca ctcgcaatca aattcagccg      3180
atagcggaac gggaaggcga ctggagtgcc atgtccggtt ttcaacaaac catgcaaatg      3240
ctgaatgagg gcatcgttcc cactgcgatg ctggttgcca acgatcagat ggcgctgggc      3300
gcaatgcgcg ccattaccga gtccgggctg cgcgttggtg cggatatctc ggtagtggga      3360
tacgacgata ccgaagacag ctcatgttat atcccgccgt taaccaccat caaacaggat      3420
tttcgcctgc tggggcaaac cagcgtggac cgcttgctgc aactctctca gggccaggcg      3480
gtgaagggca atcagctgtt gcccgtctca ctggtgaaaa gaaaaaccac cctggctcga      3540
gaaatcataa aaaatttatt tgctttgtga gcggataaca attataatag attcaattgt      3600
gagcggataa caatttcaca catctagaaa taattttatt taactttaag aaggagatat      3660
acatatgcac aaatgcgata tcaccctgca ggaaatcatc aaaaccctga attctctgac      3720
cgaacagaaa accctgtgca ccgaactgac cgttaccgac atcttcgctg cttcgaaaaa      3780
caccaccgaa aaagaaacct tctgccgtgc tgctaccgtt ctgcgtcagt tctactctca      3840
ccacgaaaaa gacacccgtt gcctgggtgc taccgctcag cagttccacc gtcacaaaca      3900
gctgatccgt ttcctgaaac gtctggaccg taacctgtgg ggtctggctg gtctgaacag      3960
ctgcccggtt aaagaagcta accagtctac cctggaaaac ttcctggaac gtctgaaaac      4020
catcatggac gaaaaagact ctaaatgctc ttcttaataa ggatccggct gctaacaaag      4080
cccgaaagga agctgagttg gctgctgcca ccgctgagca ataactagca taaccccttg      4140
gggcctctaa acgggtcttg agggttttt tgctgaaagg aggaactata tccggataat      4200
tc                                                                    4202
```